United States Patent [19]

Ford

[11] 4,214,579

[45] Jul. 29, 1980

[54] DYNAMIC SHOULDER, FOREARM, WRIST AND HAND SUPPORT

[76] Inventor: Cynthia A. Ford, 802 NW. 15, Bentonville, Ark. 72712

[21] Appl. No.: 936,301

[22] Filed: Aug. 23, 1978

Related U.S. Application Data

[63] Continuation-in-part of Ser. No. 729,223, Oct. 4, 1976, abandoned.

[51] Int. Cl.² .......................... A61F 5/40; A61F 5/04; A61F 5/10
[52] U.S. Cl. .................................. 128/94; 128/87 R; 128/77
[58] Field of Search ..................... 128/94, 87 R, 87 A, 128/77, 89 R, 90, 83

[56] References Cited

U.S. PATENT DOCUMENTS

| | | | |
|---|---|---|---|
| 594,076 | 11/1895 | Gardiner | 128/87 R |
| 1,797,057 | 4/1928 | Foulke | 128/87 R |
| 2,889,827 | 6/1959 | Basso | 128/89 R |
| 2,935,066 | 5/1960 | Holloway | 128/94 |
| 3,371,663 | 3/1968 | Apopo | 128/94 |
| 3,703,894 | 11/1972 | Galloway et al. | 128/77 |
| 3,776,225 | 12/1973 | Lonardo | 128/77 |
| 3,815,587 | 6/1974 | Guerrant | 128/77 |
| 3,815,588 | 6/1974 | Klausner | 128/94 X |

FOREIGN PATENT DOCUMENTS

1071270 10/1954 France ................................ 128/89 R

*Primary Examiner*—Robert W. Michell
*Assistant Examiner*—C. W. Shedd
*Attorney, Agent, or Firm*—Fulbright & Jaworski

[57] ABSTRACT

A shoulder, forearm, wrist and hand support is disclosed which is formed of rigid material and includes a semi-circular forearm supporting portion shaped to encompass and to exert a constant pressure on the volar surface of the forearm and to provide an edge extending laterally shaped to wrap around and support the ulna, a wrist supporting portion shaped to fit against the inner or volar surface of the wrist and support the wrist in a position of from about 9° to about 21° hyperextension, a hand supporting portion being shaped to fit against the volar surface of the hand, fingers and thumb, and to support the metacarpal-phalangeal joint in a position from about 14° to about 26° flexion, to support the proximal and distal interphalangeal joints in full extension and to hold the thumb in a position from about 29° to about 41° abduction and apposition. A strap fits snugly about the hand supporting portion and hand at the metacarpal joints thereby supporting the palmar arch, and an elastic strap having its ends secured adjacent each end of the forearm supporting portion extends over the chest, around the neck and back of the patient. The shoulder, forearm, wrist and hand are thus held in a normal position, that is, the forearm is neither pronated nor supinated, and the shoulder and elbow are free to move.

4 Claims, 8 Drawing Figures

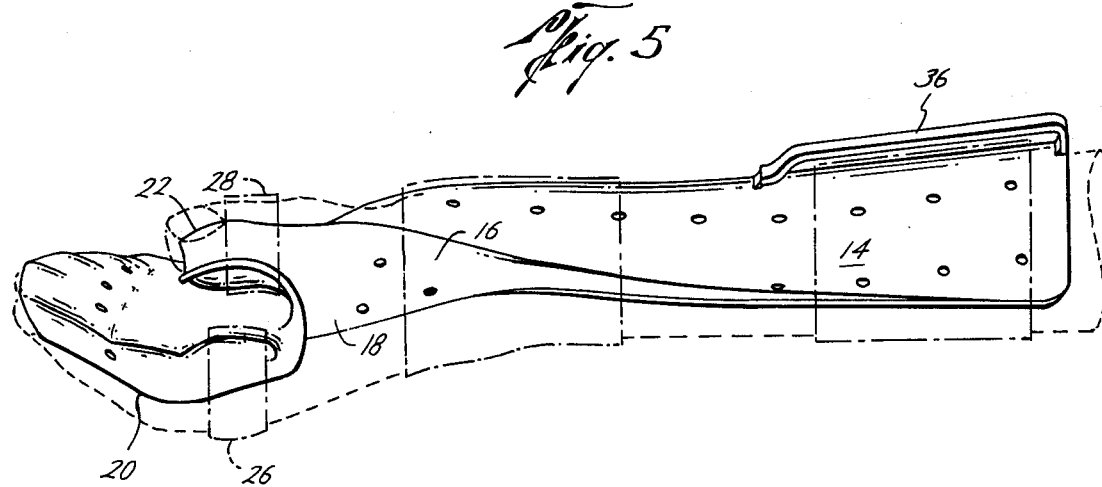
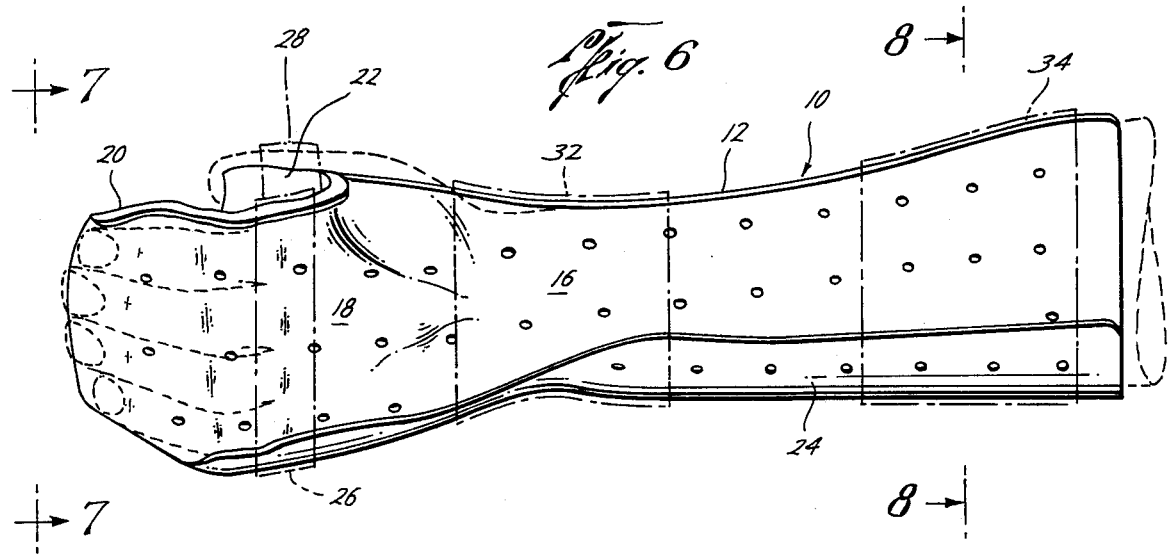
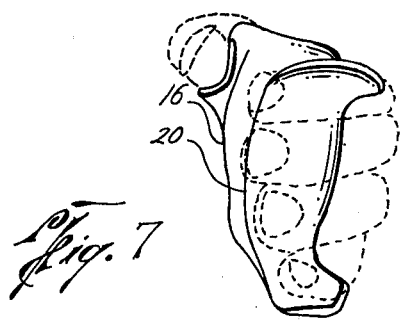
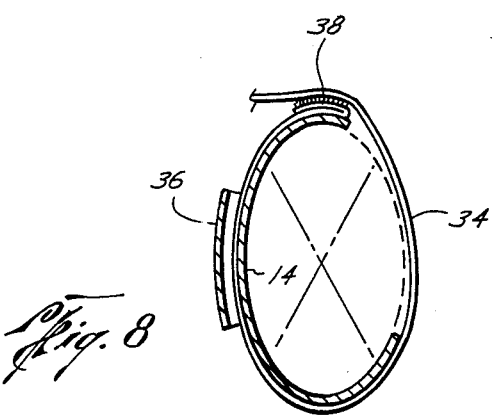

DYNAMIC SHOULDER, FOREARM, WRIST AND HAND SUPPORT

CROSS-REFERENCE TO RELATED APPLICATION

The present application is a continuation-in-part of U.S. application Ser. No. 729,223, Oct. 4, 1976, abandoned in favor of this application.

BACKGROUND OF THE INVENTION

Various slings and bandages have been employed for supporting the forearm of a patient who has had an injury or disability, particularly stroke victims. Current slings in use are static shoulder immobilizers. Total immobilization provided by these splints does adequately protect the glenohumeral joint but does nothing to promote return of normal function to stroke patients and due to their particular muscular imbalances can create additional problems.

Current splints or bandages hold the humerus in an abducted and extended position, the elbow is held at 90° flexion or more and provide little or no support at the wrist or hand. This positioning decreases the effect gravity would have on the sensory receptors within the musculature that normally protects the joint. Any decrease in sensory input to the involved joint decreases normal facilitory effects and may even inhibit normal muscular function.

An abnormal flexion synergy described by Signe Brunnstrom in *Movement Therapy in Hemiplegia* generally develops in these patients. Current splints and slings do nothing to decrease this spasticity and due to lack of support at the wrist and hand can lead to the development of contractures due to prolonged positioning of the wrist and fingers in a flexed position. In addition, no splints or slings on the market for use in protecting the glenohumeral joint provide for support of the palmar arch or the web space of the hand. This lack of support or protection can lead to destruction of the palmar arch, leading to pain and decreasing the patient's ability to have a strong, functional grasp. In addition, these splints and slings do not maintain the thumb in a position of abduction and opposition which results in the web space tending to tighten and lose its normal elasticity.

Patents known to me relating to bandages and splints are U.S. Pat. Nos. 390,176, to Lee for a Surgical Splint; 2,800,129, to H. Van Swaay for a Method of Forming Splints; and 3,815,588, to Bracha Klausner for Apparatus and Methods Relating to Support of the Forearm. In general, the splints and apparatus and methods disclosed in these patents are unsatisfactory for a number of reasons. For example, the Klausner patented structure is resilient and semi-rigid and thereby deformable by the pressure by the action of spastic or hypertonic muscles in the forearm or hand. Such muscles often exert pressure greater or at least equal to the weight of the forearm and hand. Current research supports the hypothesis that continuous firm pressure over the muscle bellies of spastic muscles will tend to inhibit or decrease the tonus of the muscle by affecting the gamma loop while materials which are resilient tend to increase spasticity. The Klausner's patent also holds the forearm in a pronated position. In hemiplegic patients, the flexion spasticity which commonly dominates in the involved upper extremity includes pronation, and thus does not lessen the possibility of a joint contraction in the pronated position. Also, in the Klausner support the shoulder and elbow are immobilized which prevents exercising the shoulder and elbow and decreases the normal sensory input to the joints and musculature's proprioceptors.

It would be highly advantageous, and the present invention is directed to, a dynamic shoulder support that allows and facilitates shoulder and elbow motion while providing sufficient protection to prevent subluxation of the glenohumeral joint, allows gravity to stimulate joint proprioceptors at the shoulder and elbow, facilitates shoulder musculature and the elbow extensors, and permits exercise including (1) shoulder abduction or adduction, (2) shoulder flexion or extension, (3) internal or external rotation at the shoulder, and (4) elbow extension or flexion and exerts a constant and firm pressure on the volar surfaces or muscle bellies of spastic muscles, thereby tending to inhibit or decrease the tonus of the muscle by affecting the gamma loop, thereby decreasing the spasticity in those muscles.

In addition, it would be highly advantageous, and the present invention is directed, to a shoulder and arm support that supports the forearm in a neutral position, neither supinated nor pronated, thereby lessening the possibility of a joint contraction in a pronated position.

SUMMARY

The present invention is therefore directed to a shoulder and arm support which avoids the foregoing disadvantages of previous splints and bandages.

More particularly, the present invention is directed to a dynamic support for supporting the shoulder and static support of the forearm, wrist and hand of a patient in which the forearm is supported in a natural position, neither supinated nor pronated, and which includes a splint formed of a rigid material and having a generally semi-circular shaped forearm supporting portion which encompasses and exerts a constant pressure on the volar surface of the forearm and provides an edge extending laterally shaped to wrap around and support the ulna; a wrist supporting portion being shaped to fit against the inner surface of the wrist and support the wrist in a position of from about 9° to about 21° hyperextension; a hand supporting portion being shaped to fit against the volar surfaces of the hand, fingers and thumb, and to support the metacarpal-phalangeal joint in a position from about 14° to about 26° flexion, to support the proximal interphalangeal at full extension, to hold the thumb in a position from about 29° to about 40° abduction and apposition; a strap which fits snugly about the hand supporting portion and the hand at the metacarpal joints, thereby supporting the palmar arch; and an elastic strap having its ends secured adjacent to each end of the forearm supporting portion and extending over the chest, around the neck and back of the patient.

The static support is made from a rigid plastic or from a lightweight material, such as metal. Preferably, the material should be such that by heating, it may be formed to fit the forearm, wrist and hand of the patient. Preferably the support is perforated to allow evaporation of prespiration from the forearm and hand.

The dynamic support permits and facilitates shoulder and elbow motion while providing sufficient protection to prevent subluxation at the glenohumeral joint and allowing gravity to stimulate joint proprioceptors at the shoulder to facilitate the shoulder musculature and elbow extension. Advantageously, the support may be used during exercises including, (1) shoulder abduction or adduction, (2) shoulder flexion or extension, (3) internal/external rotation at the shoulder, and (4) elbow extension or flexion.

It is therefore an object of the present invention to provide a support for supporting the shoulder, forearm, wrist and hand of aptient in which the forearm is supported in a normal position, that is, neither supinated nor pronated, and which permits movement of the shoulder and elbow.

A still further object of the present invention is the provision of such a support formed of a rigid material having a forearm supporting portion shaped to encompass and exert a constant pressure on the volar surface of the forearm.

Yet a further object of the present invention is the provision of such a support which has a wrist supporting portion being shaped to fit against the inner surface of the wrist and support the wrist in a desired position of hyperextension.

A further object of the present invention is the provision of such a support provided with a hand supporting portion which is shaped to fit against the volar surfaces of the hand, fingers and thumb, and to support the metacarpalphalangeal joint in a desired position of flexion, to support the proximal and distal interphalangeal joints at full extension, to hold the thumb in a desired position of abduction and apposition and to support the palmar arch.

A further object of the present invention is the provision of such a support which includes a splint made of a rigid material at ambient temperatures, but one which when heated can be shaped to fit the patient's forearm, wrist and hand.

A further object of the present invention is the provision of such a support which prevents subluxation of the glenohumeral joint but allows gravity to stimulate joint proprioceptors at the shoulder to facilitate the shoulder musculature.

Still a further object of the present invention is the provision of such a support which the patient can wear during exercising the shoulder and elbow.

Other and further objects, features and advantages appear throughout.

A BRIEF DESCRIPTION OF THE DRAWINGS

FIG. 5 is a top view of the splint illustrated in FIGS. 1-4, FIG. 6 is a side view of the splint illustrated in FIGS. 1-5, FIG. 7 is a view taken along the line 7—7 of FIG. 6, and FIG. 8 is a view taken along the line 8—8 of FIG. 6.

DESCRIPTION OF PREFERRED EMBODIMENTS

Figure 1:
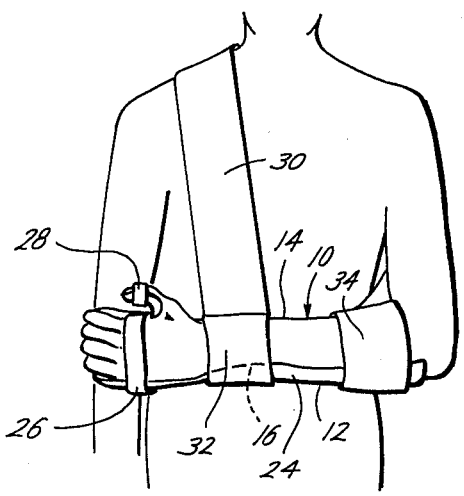
FIG. 1 is a front view of a patient wearing the dynamic shoulder support of the present invention.

Referring to the drawings, and particularly to FIG. 1, the dynamic support is indicated by the reference numeral 10 and is illustrated supporting the shoulder, forearm, wrist and hand of a patient.

Referring now to FIGS. 5 and 6, the support 10 includes a splint 12 formed of a rigid material and having a forearm supporting portion 14, a wrist supporting portion 16 and a hand supporting portion 18 which includes finger supporting portions 20 and thumb supporting portion 22. The splint 12 may be formed of any rigid material, such as the various plastics which are rigid or from a lightweight material such as metal. It is essential that the splint be formed of a material which is not resilient and which will not deform due to pressures exerted by muscle bellies or volar surfaces of the forearm and of the wrist, hand, fingers and thumb when in use. Preferably, the splint is made of a thermoplastic material which is rigid at ambient temperatures, but upon heating to temperatures well above ambient will soften so that the splint can be shaped as desired or further shaped to fit an individual forearm, wrist and hand of the patient. The term "rigid" as used herein means a material which will not deform under conditions of use. For example, materials when formed into splints which have a tensil strength to withstand at least about 4,000 lb/in$^2$ and, preferably materials which will withstand from about 4,000 lb/in$^2$ to 6,000 lb/in$^2$ as tested under FDA testing procedures are satisfactory. Among thermoplastic orthopedic materials which can be used are Orthoplast ® and Theraplast ®, both of which are readily available from Luba Medical Supply Company. Since there are many suitable materials for a rigid splint readily available on the market, no further description thereof is deemed necessary or given.

The forearm supporting portion 14 is generally semicircularly shaped to encompass and to exert a constant pressure on the volar surface or inner surface of the forearm, and to provide an edge 24 which extends laterally from the lower portion of the forearm supporting portion 14 and is shaped to wrap around and support the ulna. It is unnecessary that the lateral edge 24 completely wrap around the ulna, but it only needs to wrap around it sufficiently to support it. Perferably, it should wrap around at least one-third of the ulna and should generally be curved to fit about and support the lower portion of the forearm.

The wrist supporting portion 16 is shaped to fit against the inner or volar surface of the wrist and support the wrist in a position of from about 9° to about 21° hyperextension and, preferably, 15° as illustrated in the drawing.

The hand supporting portion 18 is shaped to fit against the volar surface of the hand, and the finger supporting portion 20 and thumb supporting portion 22 are shaped to fit against the volar surfaces of the fingers and the thumb, respectively. The hand supporting portion supports the metacarpal-phalangeal joint in a position of from about 14° to about 26° flexion and, ideally, 19° flexion, the finger supporting portion 20 supports the proximal and distal interphalangeal joints at full extension, and the thumb supporting portion 22 supports the thumb in a position from about 29° to about 41° abduction and apposition, and preferably, 35°.

A strap 26 is provided which fits snugly about the hand supporting portion 18 and the hand of the patient at the metacarpal joints which thereby supports the palmar arch by holding it against the hand supporting portion 18.

A strap 28 is provided which fits snugly about the thumb supporting portion 22 and the thumb of the patient so that the thumb is held and supported in the position from about 29° to about 41° abduction, as previously described.

Figure 2:
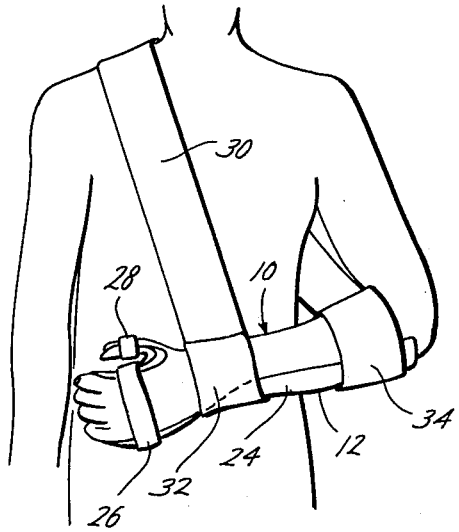
FIG. 2 is a view similar to that of FIG. 1, illustrating the patient moving his arm and shoulder in a sidewise direction or abduction and adduction.
Figure 3:
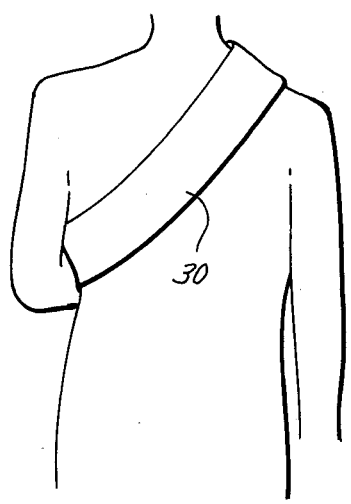
FIG. 3 is a back view of FIG. 1.

As best illustrated in FIGS. 1, 2 and 3, an elasticized band 30 is provided which extends over the chest, around the neck and the back of the patient and has one end loop 32 secured about the forearm supporting portion 14 adjacent the wrist supporting portion 16 and has its other end loop 34 secured adjacent the distal end of the forearm supporting portion 14. The end loop 32 loops about the splint 12 and firmly holds the wrist and outer forearm portion against the splint 12 as does the end loop 34 which loops around the forearm and the splint and securely holds the forearm against the splint, as illustrated. These loops may be separate or be the ends of the elastic strap or band 30. If separate, they should be elastic loops and therefore having some give which further inhibits the spastic wrist and long finger flexors by acting on the gamma loop of the wrist and finger extensors. The wrist and finger extensors are inhibited due to the spasticity in the flexors; whereas, they should be facilitated with the conditions in the splint. Thus, preferably the end loops 32 and 34 should be elastic with some give.

Preferably, quick makeup and release connectors are provided for the loop ends 32 and 34, as best illustrated in FIG. 8 and which are here shown as Velcro ® fasteners 36. Preferably, the same type of quick makeup and release connectors are utilized for forming the loops 26 and 28. Any type of desired connectors may be used.

In addition, to prevent slipping of the loop end 34 on the distal end of the forearm supporting portion of the splint 12 a loop 38 is provided on the inner surface of the latter.

Figure 4:
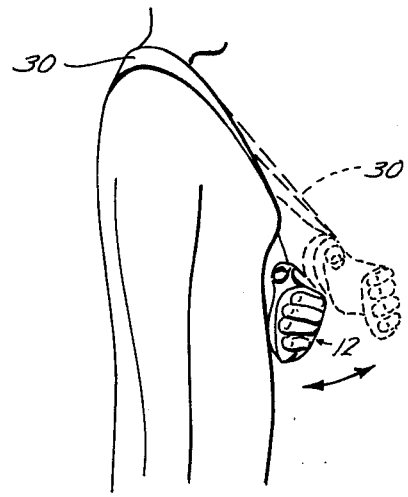
FIG. 4 is a side view of FIG. 1 illustrating in-and-out movement of the arm of the patient or flexion and extension.

In use, the support 10 is placed on the patient's forearm, wrist, hand and thumb, with the loops 26 and 28, the strap with its loop ends 32 and 34 in the positions illustrated in FIGS. 1-4. It is seen that the forearm is held in a natural or normal position, that is, in a general vertical plane, and is neither supinated nor pronated, which lessens the possibility of a joint contraction which would occur in a pronated position. As illustrated in FIGS. 2 and 4, the support 10 allows and facilitates shoulder and elbow motion while providing sufficient protection to prevent subluxation of the glenohumeral joint, allows gravity to stimulate joint proprioceptors at the shoulder, facilitates shoulder musculature and permits exercises, including, (1) shoulder abduction or adduction (FIG. 2), (2) shoulder flexion or extension (FIG. 4), (3) internal or external rotation at the shoulder, not illustrated, and, (4) elbow extension or flexion (FIG. 2).

In addition, the rigid forearm supporting portion 14 exerts a constant and firm pressure on the volar surfaces or muscle bellies of spastic muscles, thereby tending to inhibit or decrease the tonus of the muscle by affecting the gamma loop, thereby decreasing the spasticity in those muscles. Also, wrist and finger flexors, which tend to be spastic, are inhibited.

The present invention therefore is well-suited and adapted to attain the objects and ends and has the advantages and features mentioned as well as others inherent therein.

While presently preferred examples of the invention have been given for the purpose of disclosure, changes may be made therein which are within the spirit of the invention as defined by the scope of the appended claims.

What is claimed is:

1. A dynamic support for supporting the shoulder, forearm, wrist and hand of a patient comprising,
   a splint molded from a thermoplastic material rigid enough not to be deformable at ambient temperatures by pressures exerted by muscle bellies and volar surfaces of the forearm, the wrist and the hand, fingers and thumb, the splint having a forearm supporting portion, a wrist supporting portion, and a hand supporting portion,
   the forearm supporting portion's top being open and its bottom being generally semi-circularly shaped to encircle the ulna side of the forearm and to encompass and to exert a constant pressure on the volar surface of the forearm, said forearm support having an edge extending laterally and shaped to wrap around and support the ulna, while placing no inhibiting pressure on the forearm,
   the wrist supporting portion being shaped to fit against the inner surface of the wrist and support the wrist in a position of from about 9° to about 21° hyperextension,
   the hand supporting portion being shaped to fit against the volar surfaces of the hand, fingers and thumb, and to support the metacarpal-phalangeal joints in a position from about 14° to about 26° flexion, to support the proximal and distal interphalangeal joints at full extension, and having a thumb supporting portion in a position from about 29° to about 41° abduction and opposition,
   a first strap adapted to snugly fit about the hand supporting portion and the hand at the metacarpal joints thereby supporting the palmar arch,
   a second strap adapted to fit about the thumb and thumb supporting portion, and
   an elastic strap having forward and rearward elastic loops at its lower ends disposed about each end of the forearm supporting portion, when providing support said elastic strap extends diagonally from the forward loop in front of the chest, over the shoulder opposite the arm being supported, across the back and between the upper arm and the rib cage of the patient to the rearward loop,
   the elastic strap extending as described above supports the forearm, wrist and hand in a position such that the vola of the hand being supported faces toward the patient's body thus permitting the patient to move the shoulder and elbow of the arm being supported,
   the elastic loops are provided with quick makeup and release connectors at their ends so as to be adjustably securable and thereby capable of firmly holding the forearm against the forearm supporting portion.

2. The dynamic support of claim 1 where, the support is provided with perforations.

3. The dynamic support of claim 1 where,
   the wrist supporting portion supports the wrist at about 15° hyperextension,
   the hand supporting portion supports the metacarpal-phalangeal joint at about 19° flexion and
   the thumb supporting portion holds the thumb at about 35° abduction and opposition.

4. The dynamic shoulder support of claim 3 where, the support is provided with perforations.

* * * * *

UNITED STATES PATENT OFFICE
CERTIFICATE OF CORRECTION

Patent No. 4,214,579          Dated    July 29, 1980

Inventor(s)  Cynthia A. Ford

It is certified that error appears in the above-identified patent and that said Letters Patent are hereby corrected as shown below:

Column 3, Line 6, change -- apient -- to -- "patient" --;

Column 4, Line 40, change -- Perferably -- to "Preferably"--;

Column 6, Line 48, change -- vola -- to --"volva"--;

Column 6, Line 50, after -- and --, add -- "the"--

Signed and Sealed this

Eleventh Day of November 1980

[SEAL]

Attest:

SIDNEY A. DIAMOND

Attesting Officer

Commissioner of Patents and Trademarks